(12) United States Patent
Qi et al.

(10) Patent No.: US 11,215,543 B1
(45) Date of Patent: Jan. 4, 2022

(54) ROCK MASS SHEAR TEST SYSTEM FOR HIGH-ENERGY ACCELERATOR COMPUTED TOMOGRAPHY (CT) SCANNING

(71) Applicant: INSTITUTE OF GEOLOGY AND GEOPHYSICS, CHINESE ACADEMY OF SCIENCES, Beijing (CN)

(72) Inventors: Shengwen Qi, Beijing (CN); Bowen Zheng, Beijing (CN); Xiaolin Huang, Beijing (CN); Songfeng Guo, Beijing (CN); Ning Liang, Beijing (CN); Yu Zou, Beijing (CN); Guangming Luo, Beijing (CN); Luqing Zhang, Beijing (CN); Haijun Zhao, Beijing (CN); Lei Xue, Beijing (CN); Zhiqing Li, Beijing (CN); Jie Guo, Beijing (CN); Libo Jiang, Beijing (CN); Xin Wang, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/361,332

(22) Filed: Jun. 29, 2021

(30) Foreign Application Priority Data

Nov. 11, 2020 (CN) .......................... 202011256870.7

(51) Int. Cl.
*G01N 3/24* (2006.01)
*G01N 3/06* (2006.01)
(Continued)

(52) U.S. Cl.
CPC ................. *G01N 3/24* (2013.01); *G01N 3/06* (2013.01); *G01N 23/046* (2013.01); *G01N 23/06* (2013.01);
(Continued)

(58) Field of Classification Search
CPC ............ G01N 3/24; G01N 3/06; G01N 23/06; G01N 23/046; G01N 33/24;
(Continued)

(56) References Cited

U.S. PATENT DOCUMENTS

2019/0313984 A1   10/2019  Sun et al.

FOREIGN PATENT DOCUMENTS

| CN | 102478473 A | 5/2012 |
| CN | 202735156 U | 2/2013 |

(Continued)

OTHER PUBLICATIONS

Xiaolin Huang, et al.. Particle Crushing of a Filled Fracture During Compression and Its Effect on Stress Wave Propagation, Journal of Geophysical Research: Solid Earth, 2018, pp. 5559-5587,123.
(Continued)

*Primary Examiner* — Jonathan M Dunlap
(74) *Attorney, Agent, or Firm* — Bayramoglu Law Offices LLC

(57) ABSTRACT

A rock mass shear test system for high-energy accelerator computed tomography (CT) scanning includes double horizontal loading devices, a first bearing device for bearing a static shear box, a second bearing device for bearing a dynamic shear box, and a normal loading device, etc. In the test, the double horizontal loading devices simultaneously apply an identical loading force to the rock mass, and the normal loading device applies a shear force to the rock mass. The double horizontal loading devices are provided in parallel and spaced apart, a loading force is applied in the
(Continued)

horizontal direction, and a shear force is applied in the vertical direction, so that the loading cylinder and the rock mass sample are effectively prevented from interfering with each other during the accurate scanning process of the shearing progressive failure process of the rock mass.

16 Claims, 2 Drawing Sheets

(51) Int. Cl.
*G01N 23/046* (2018.01)
*G01N 23/06* (2018.01)
*G01N 33/24* (2006.01)

(52) U.S. Cl.
CPC ..... *G01N 33/24* (2013.01); *G01N 2203/0025* (2013.01); *G01N 2203/0048* (2013.01); *G01N 2203/0064* (2013.01); *G01N 2203/0066* (2013.01); *G01N 2203/0641* (2013.01); *G01N 2223/04* (2013.01); *G01N 2223/419* (2013.01)

(58) Field of Classification Search
CPC ... G01N 2203/0048; G01N 2203/0066; G01N 2203/0064; G01N 2203/0025; G01N 2223/419
See application file for complete search history.

(56) References Cited

FOREIGN PATENT DOCUMENTS

| | | |
|---|---|---|
| CN | 103822833 A | 5/2014 |
| CN | 203949829 U | 11/2014 |
| CN | 106290023 A | 1/2017 |
| CN | 106525575 A | 3/2017 |
| CN | 109975106 A | 7/2019 |
| CN | 209280475 U | 8/2019 |
| JP | 2018159700 A | 10/2018 |

OTHER PUBLICATIONS

Chang Hong, et al., Development and Application of Experiment System for Soil-Hydraulic Structure Interface, Industrial Construction, 2013, pp. 71-75, vol. 43 No.6.

Guo Jie, et al., Application and Improvement of Rock and Soil Mass Shear Test Device, Chinese Journal of Underground Space and Engineering, 2011, pp. 1143-1147, vol. 7 No.6.

ROCK MASS SHEAR TEST SYSTEM FOR HIGH-ENERGY ACCELERATOR COMPUTED TOMOGRAPHY (CT) SCANNING

CROSS REFERENCE TO THE RELATED APPLICATIONS

This application is based upon and claims priority to Chinese Patent Application No. 202011256870.7, filed on Nov. 11, 2020, the entire contents of which are incorporated herein by reference.

TECHNICAL FIELD

The present invention belongs to the technical field of tests of rock mechanics, and specifically relates to a rock mass shear test system for high-energy accelerator computed tomography (CT) scanning.

BACKGROUND

The rock mass is a geological body composed of rock blocks and structural surfaces. The shear strength characteristics of the rock mass are a key index to evaluate the stability thereof. Under the action of a shearing stress, the rock mass will undergo a progressive failure process of incubation, initiation, propagation and penetration of cracks. The quantitative characterization of the shearing progressive failure process is very important for determining the shear strength characteristics of the rock mass.

The existing research is mainly carried out by using a laboratory test and a numerical simulation. In the laboratory test, the time and space information of the generation and development of cracks in the shearing progressive failure process of the rock mass can be acquired indirectly by using the shear tester in combination with acoustic emission equipment, but the dynamic evolution process of the cracks inside the rock mass cannot be directly characterized. In the numerical simulation, the growth process of the cracks inside the rock mass is described by using a finite element method or a discrete element method in combination with a modeling parameter trial and error method. However, due to the multi-solution of the numerical simulation method, the dynamic damage and failure process inside the rock mass cannot be truly reflected. Therefore, the aforementioned two methods have limitations in deeply understanding the shear strength characteristics of the rock mass.

In order to overcome the above shortcomings, it is urgently desirable to develop a rock mass shear test platform for high-energy accelerator CT scanning to quantitatively characterize the shearing progressive failure process of the rock mass. The rock mass shear test technology and the high-energy accelerator CT scanning technology can be combined to realize the visualization of incubation, initiation, propagation and penetration of cracks during the shearing progressive shear failure process of the rock mass. In the existing rock mass shear test system for high-energy accelerator CT scanning, the loading frame applies a shear force in the horizontal direction and a pressure or tension in the vertical direction. The loading cylinder in the loading device or shearing device is inevitably disposed on the outer side of the rock mass sample. When the high-energy accelerator CT scanning is performed, the loading cylinder will appear in the field of view of the scanned rock mass sample. This will lead to inaccurate scanning results and make it impossible to scan the rock mass sample in all directions during the shear test, thereby failing to meet the requirements for visualization of the shearing progressive failure process of the rock mass sample.

SUMMARY

In order to solve the above-mentioned problem in the prior art, that is, in order to realize the accurate scanning of the shearing progressive failure process of the rock mass, the present invention provides a rock mass shear test system for high-energy accelerator CT scanning. The test system comprises a shear box for accommodating a rock mass sample, a bearing device for supporting the shear box, and a shear loading device; the shear box comprises a static shear box and a dynamic shear box; the static shear box and the dynamic shear box are provided opposite to each other from left to right; the static shear box comprises a first rectangular frame, and the dynamic shear box includes a second rectangular frame; the second rectangular frame is opposite to the first rectangular frame;

the bearing device includes a first bearing device and a second bearing device; the first bearing device is provided on an outer side of the static shear box; the first rectangular frame is fixedly provided on an inner side of the first bearing device; the first bearing device and the first rectangular frame constitute a left-half accommodating cavity with a right opening; the second bearing device is provided on an outer side of the dynamic shear box; the second rectangular frame is fixedly provided on an inner side of the second bearing device; the second bearing device is provided with a protrusive structure extending into the second rectangular frame; the second bearing device and the second rectangular frame constitute a right-half accommodating cavity with a left opening;

the shear loading device includes a horizontal loading device and a normal loading device; the horizontal loading device includes a first horizontal loading device and a second horizontal loading device; the first horizontal loading device includes a first horizontal loading frame and a first horizontal loading cylinder; the first horizontal loading frame is provided with a first rectangular through hole; an upper side surface of the first bearing device is connected to a left side wall of the first rectangular through hole; the first horizontal loading cylinder is connected to a right side wall of the first rectangular through hole, and is configured to apply a first horizontal loading force to the second bearing device under the action of a hydraulic pressure; the second horizontal loading device includes a second horizontal loading frame and a second horizontal loading cylinder; the second horizontal loading frame is provided with a second rectangular through hole; a middle side surface of the first bearing device is connected to a left side wall of the second rectangular through hole; the second horizontal loading cylinder is connected to a right side wall of the second rectangular through hole, and is configured to apply a second horizontal loading force to the second bearing device under the action of a hydraulic pressure; the normal loading device is provided under the second rectangular frame; a movable end of the normal loading device is provided in contact with the second rectangular frame;

during a shearing process, the first horizontal loading cylinder and the second horizontal loading cylinder apply a horizontal loading force to the rock mass sample through the second bearing device; the normal loading device, under the action of a driving force, presses the second rectangular frame, the second bearing device and a rock mass sample placed inside the second rectangular frame to move upward relative to a rock mass sample placed inside the first rectangular frame, so as to perform a shear test of the rock mass sample.

In some preferred embodiments, the test system further includes a high-energy accelerator CT scanning system and a rotating device; the high-energy accelerator CT scanning system includes a ray source device and a detector device; the ray source device and the detector device are respectively provided on both sides of the rock mass sample, and are configured to detect a progressive failure process of incubation, initiation, propagation and penetration of cracks of the rock mass sample in the shear test;

a height of the ray source device is h, a height of the first horizontal loading cylinder is h1, and a height of the second horizontal loading cylinder is h2, where h E (h2, h1);

the rotating device is provided under the bearing device and the normal loading device; the rotating device is driven by a rotating power device to drive the loading device and the bearing device to rotate with the shear box, and cooperate with the high-energy accelerator CT scanning system to accurately acquire time and space information of generation and development of cracks in a shearing progressive failure process of a rock mass.

In some preferred embodiments, the first horizontal loading cylinder includes a first piston assembly and a first cylinder block assembly; one end of the first piston assembly away from the second bearing device is fixedly provided on the first horizontal loading frame, and the other end of the first piston assembly is provided inside the first cylinder block assembly; a first loading cavity is provided between the first piston assembly and the first cylinder block assembly; the first loading cavity is configured to control a loading force of the first cylinder block assembly on the second bearing device through the injection/return of hydraulic oil; a first static pressure support cavity is provided at an end of the first cylinder block assembly away from the first piston assembly; the first static pressure support cavity is configured to control the loading force of the first cylinder block assembly on the second bearing device through the injection/return of the hydraulic oil, and reduce a friction generated between the first cylinder block assembly and the second bearing device due to the vertical movement of the second bearing device during the loading process;

a distance from a side of the first static pressure support cavity away from the second bearing device to the first piston assembly is smaller than a distance from a side of the first cylinder block assembly away from the first piston assembly to the first piston assembly;

a first vertical limiting device and a second vertical limiting device are respectively provided on both sides of the first cylinder block assembly; the first vertical limiting device and the second vertical limiting device are symmetrically provided relative to a length axis of the first cylinder block assembly; the first vertical limiting device and the second vertical limiting device are fixedly provided on an upper part of the second bearing device, and the first vertical limiting device and the second vertical limiting device are provided in contact with the first cylinder block assembly.

In some preferred embodiments, the second horizontal loading cylinder and the first horizontal loading cylinder are provided in parallel;

the second horizontal loading cylinder includes a second piston assembly and a second cylinder block assembly; one end of the second piston assembly away from the second bearing device is fixedly provided on the second horizontal loading frame, and the other end of the second piston assembly is provided inside the second cylinder block assembly; a second loading cavity is provided between the second piston assembly and the second cylinder block assembly; the second loading cavity is configured to control a loading force of the second cylinder block assembly on the second bearing device through the injection/return of hydraulic oil; a second static pressure support cavity is provided at an end of the second cylinder block assembly away from the second piston assembly; the second static pressure support cavity is configured to control the loading force of the second cylinder block assembly on the second bearing device through the injection/return of the hydraulic oil, and reduce a friction generated between the second cylinder block assembly and the second bearing device due to the vertical movement of the second bearing device during the loading process;

a distance from a side of the second static pressure support cavity away from the second bearing device to the second piston assembly is smaller than a distance from a side of the second cylinder block assembly away from the second piston assembly to the second piston assembly;

a third vertical limiting device and a fourth vertical limiting device are respectively provided on both sides of the second cylinder block assembly; the third vertical limiting device and the fourth vertical limiting device are symmetrically provided relative to a length axis of the second cylinder block assembly; the third vertical limiting device and the fourth vertical limiting device are fixedly provided on a lower part of the second bearing device, and the third vertical limiting device and the fourth vertical limiting device are provided in contact with the second cylinder block assembly.

In some preferred embodiments, the first bearing device includes a first structure, a second structure and a third structure, which are provided in sequence;

the static shear box further includes a first limiting device and a second limiting device; the first limiting device and the second limiting device are respectively provided on an upper side and a lower side of the first rectangular frame; the first limiting device is fixedly provided on an inner side of the first structure; the second limiting device is fixedly provided on an inner side of the third structure;

a rectangular protrusive structure is provided on an inner side of the second structure, and the rectangular protrusive structure is adapted to the rectangular through hole of the first rectangular frame;

the first structure, the second structure and the third structure are integrally formed or fixedly connected.

In some preferred embodiments, the first bearing device further includes a fourth structure; the fourth structure is horizontally provided on the inner side of the third structure; the fourth structure forms an L-shaped structure with the first structure, the second structure and the third structure; and the normal loading device is fixedly provided on the top of the fourth structure.

In some preferred embodiments, the first limiting device is a first limiting cushion block; the second limiting device is a second limiting cushion block; the first limiting cushion block and the second limiting cushion block are configured to fix the static shear box and provide a reaction force to the static shear box during the shearing process;

a horizontal length of the first limiting cushion block and a horizontal length of the second limiting cushion block are not greater than a horizontal length of the first rectangular frame.

In some preferred embodiments, a vertical length of a lower side frame of the second rectangular frame is greater than a vertical length of an upper side frame of the second rectangular frame.

In some preferred embodiments, the first horizontal loading frame and the second horizontal loading frame have an identical structure; and each of the first horizontal loading frame and the second horizontal loading frame is a self-balancing loading frame.

In some preferred embodiments, a first adjusting plate is provided on a side of the first bearing device adjacent to the rock mass sample;

a second adjusting plate is provided on a side of the second bearing device adjacent to the rock mass sample;

each of the first adjusting plate and the second adjusting plate is a rectangular plate; and the first adjusting plate and the second adjusting plate are respectively adapted to the interior of the first rectangular frame and the interior of the second rectangular frame.

The present invention proposes double horizontal loading devices for applying a horizontal loading force and a normal loading device for applying a shear force. In the shear test of a rock mass, a horizontal loading steel frame and a second bearing device apply a loading force to the rock mass sample, and the normal loading device applies a shear force to the rock mass sample through a second rectangular frame. Such a design satisfies the requirements of the shear test while staggering the cylinder in the shear loading device and the rock mass sample. It is ensured that a high-energy accelerator CT scanning system accurately scans the incubation, initiation, propagation and penetration of cracks in the shearing progressive failure process of the rock mass, so as to acquire the time and space information of the generation and development of the cracks in this process.

BRIEF DESCRIPTION OF THE DRAWINGS

Other features, objectives and advantages of the present invention will become more apparent upon reading the detailed description of the non-restrictive embodiments with reference to the following accompanying drawings.

Figure 1:
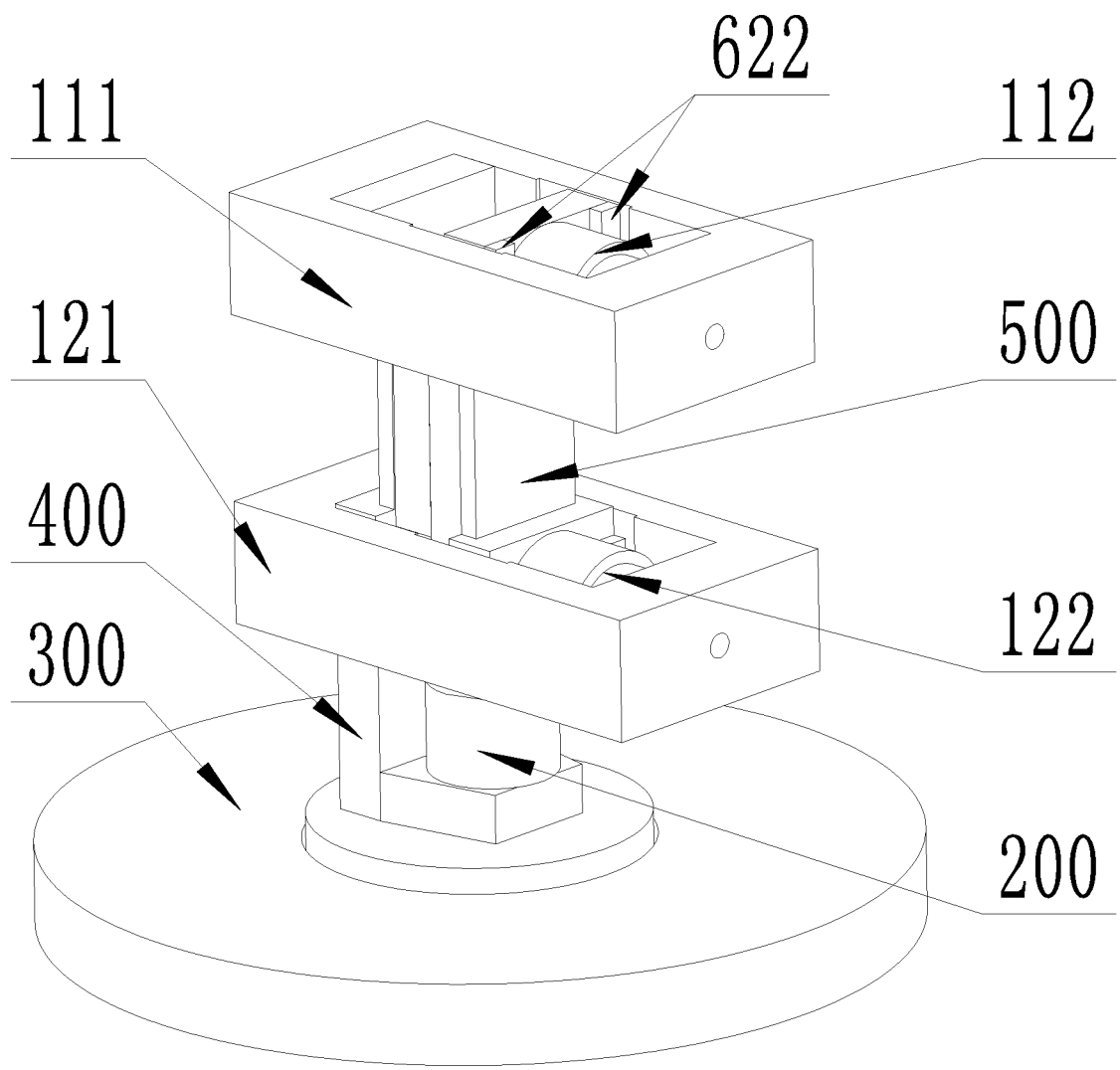
FIG. 1 is a stereoscopic view of a specific embodiment of a rock mass shear test system for high-energy accelerator CT scanning according to the present invention.

Reference Numerals: 111. first horizontal loading frame; 112. first horizontal loading cylinder; 1121. first piston assembly; 1122. first loading cavity; 1123. first cylinder block assembly; 1124. first static pressure support cavity; 121. second horizontal loading frame; 122. second horizontal loading cylinder; 1221. second piston assembly; 1222. second loading cavity; 1223. second cylinder block assembly; 1224. second static pressure support cavity; 200. normal loading device; 300. rotating device; 400. first bearing device; 410. first adjusting plate; 500. second bearing device; 510. second adjusting plate; 611. first rectangular frame; 612. first limiting cushion block; 613. second limiting cushion block; 621. second rectangular frame; 622. vertical limiting device; and 700. rock mass sample.

DETAILED DESCRIPTION OF THE EMBODIMENTS

The preferred implementations of the present invention are described below with reference to the accompanying drawings. Those skilled in the art should understand that the implementations herein are merely intended to explain the technical principles of the present invention, rather than to limit the protection scope of the present invention.

The present invention provides a rock mass shear test system for high-energy accelerator CT scanning. The test system includes a shear box for accommodating a rock mass sample, a bearing device for supporting the shear box, and a shear loading device. The shear box includes a static shear box and a dynamic shear box. The static shear box and the dynamic shear box are provided opposite to each other from left to right. The static shear box includes a first rectangular frame, and the dynamic shear box includes a second rectangular frame. The second rectangular frame is opposite to the first rectangular frame. The bearing device includes a first bearing device and a second bearing device. The first bearing device is provided on an outer side of the static shear box. The first rectangular frame is fixedly provided on an inner side of the first bearing device. The first bearing device and the first rectangular frame constitute a left-half accommodating cavity with a right opening. The second bearing device is provided on an outer side of the movable shear box. The second rectangular frame is fixedly provided on an inner side of the second bearing device. The second bearing device is provided with a protrusive structure extending into the second rectangular frame. The second bearing device and the second rectangular frame constitute a right-half accommodating cavity with a left opening. The shear loading device includes a horizontal loading device and a normal loading device. The horizontal loading device includes a first horizontal loading device and a second horizontal loading device. The first horizontal loading device includes a first horizontal loading frame and a first horizontal loading cylinder. The first horizontal loading frame is provided with a first rectangular through hole. An upper side surface of the first bearing device is connected to a left side wall of the first rectangular through hole. The first horizontal loading cylinder is connected to a right side wall of the first rectangular through hole, and is configured to apply a first horizontal loading force to the second bearing device under the action of a hydraulic pressure. The second horizontal loading device includes a second horizontal loading frame and a second horizontal loading cylinder. The second horizontal loading frame is provided with a second rectangular through hole. A middle side surface of the first bearing device is connected to a left side wall of the second rectangular through hole. The second horizontal loading cylinder is connected to a right side wall of the second rectangular through hole, and is configured to apply a second horizontal loading force to the second bearing device under the action of a hydraulic pressure. The normal loading device is provided under the second rectangular frame, and a movable end of the normal loading device is provided in contact with the second rectangular frame. During a shearing process, the first horizontal loading cylinder and the second horizontal loading cylinder apply a horizontal loading force to the rock mass sample through the second bearing device. The normal loading device, under the action of a driving force, presses the second rectangular frame, the second bearing device and a rock mass sample placed inside the second rectangular frame to move upward relative to a rock mass sample placed inside the first rectangular frame, so as to perform a shear test of the rock mass sample.

The present invention is further described with reference to the accompanying drawings and specific embodiments.

Figure 2:
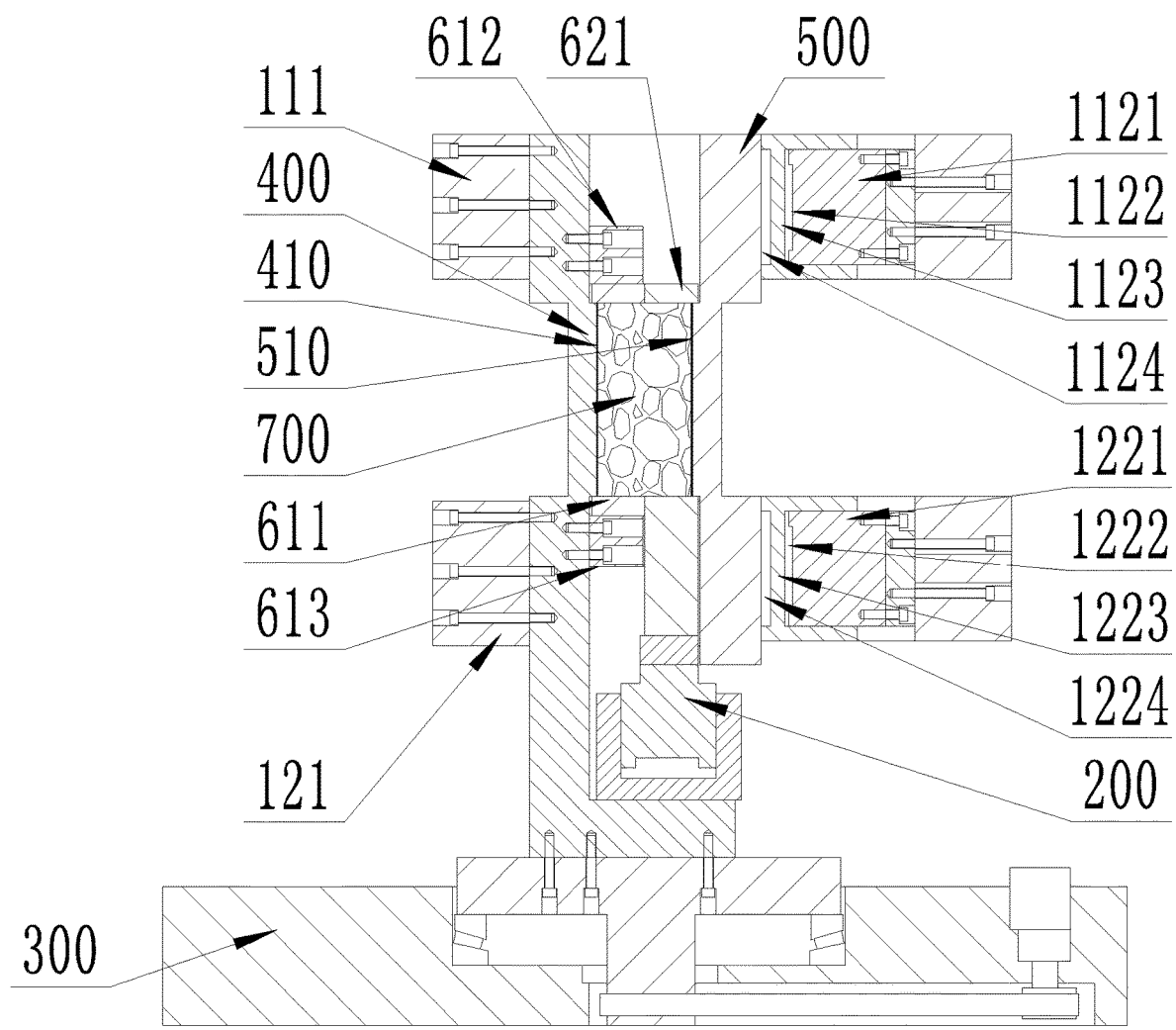
FIG. 2 is a sectional view of a specific embodiment of a rock mass shear test system for high-energy accelerator CT scanning according to the present invention.

The present invention provides a rock mass shear test system for high-energy accelerator CT scanning, as shown in FIGS. 1 and 2. FIG. 1 is a stereoscopic view of a specific embodiment of a rock mass shear test system for high-energy accelerator CT scanning according to the present invention. FIG. 2 is a sectional view of a specific embodiment of a rock mass shear test system for high-energy accelerator CT scanning according to the present invention. The test system includes a shear box for accommodating a rock mass sample, a bearing device for supporting the shear box, and a shear loading device. The shear box includes a static shear box and a dynamic shear box. The static shear box and the dynamic shear box are provided opposite to each other from left to right to cooperate with a normal loading device to perform a shear test of the rock mass sample. The static shear box includes a first rectangular frame 611, and the dynamic shear box includes a second rectangular frame 621. The second rectangular frame is opposite to the first rectangular frame to form a side frame for accommodating a rock mass sample 700.

The bearing device includes a first bearing device 400 and a second bearing device 500. The first bearing device is provided on an outer side of the static shear box. The first rectangular frame 611 is fixedly provided on an inner side of the first bearing device, and a section of the first bearing device at the rock mass sample and the first rectangular frame constitute a left-half accommodating cavity with a right opening, which serves as a cavity of the static shear box. The second bearing device is provided on an outer side of the movable shear box. The second rectangular frame 621 is fixedly provided on an inner side of the second bearing device. The second bearing device is provided with a protrusive structure extending into the second rectangular frame. The second bearing device and the second rectangular frame constitute a right-half accommodating cavity with a left opening, which serves as a cavity of the dynamic shear box. In this way, when the normal loading device 200 presses the second rectangular frame, the second bearing device and the second rectangular frame are driven to move synchronously through the protrusive structure to realize the shear test of the rock mass sample inside the dynamic shear box.

The shear loading device includes a horizontal loading device and a normal loading device. The horizontal loading device includes a first horizontal loading device and a second horizontal loading device. The first horizontal loading device includes a first horizontal loading frame 111 and a first horizontal loading cylinder 112. The first horizontal loading frame is provided with a first rectangular through hole. An upper left side surface of the first bearing device 400 is fixedly connected to a left side wall of the first rectangular through hole. The first horizontal loading cylinder is connected to a right side wall of the first rectangular through hole, and is configured to apply a first horizontal loading force to the second bearing device 500 under the action of a hydraulic pressure. The second horizontal loading device includes a second horizontal loading frame 121 and a second horizontal loading cylinder 122. The second horizontal loading frame is provided with a second rectangular through hole. A middle left side surface of the first bearing device is fixedly connected to a left side wall of the second rectangular through hole. The second horizontal loading cylinder is connected to a right side wall of the second rectangular through hole, and is configured to apply a second horizontal loading force to the second bearing device under the action of a hydraulic pressure. The normal loading device is provided under the second rectangular frame 621, and a movable end of the normal loading device 200 is provided in contact with the second rectangular frame, so as to drive the dynamic shear box to move. During a shearing process, the first horizontal loading cylinder and the second horizontal loading cylinder apply a horizontal loading force to the rock mass sample through the second bearing device. The normal loading device, under the action of a driving force, presses the second rectangular frame, the second bearing device and a rock mass sample placed inside the second rectangular frame to move upward relative to a rock mass sample placed inside the first rectangular frame 611, so as to perform a shear test of the rock mass sample.

The shear box is provided with a high-energy accelerator CT scanning system (not shown in the figure) on a side thereof and a rotating device 300 on the bottom thereof. The high-energy accelerator CT scanning system includes a ray source device and a detector device. The ray source device and the detector device are respectively provided on both sides of the rock mass sample to detect a progressive failure process of incubation, initiation, propagation and penetration of cracks of the rock mass sample in the shear test. The height of the ray source device is h, the height of the first horizontal loading cylinder is h1, and the height of the second horizontal loading cylinder is h2, where h∈(h2, h1). The rotating device is provided under the bearing device and the normal loading device. The rotating device is driven by a rotating power device to drive the loading device and the bearing device to rotate with the shear box, and cooperate with the high-energy accelerator CT scanning system to accurately acquire the time and space information of the generation and development of the cracks in the shearing progressive failure process of the rock mass.

It should be noted that in the rock mass shear test system for high-energy accelerator CT scanning as disclosed in the prior art, the loading frame applies a shear force in the horizontal direction and a pressure or tension in the vertical direction. The loading cylinder in the loading device or shearing device is disposed on the outside of the rock mass sample. When the high-energy accelerator CT scanning is performed, the loading cylinder will appear in the field of view of the scanned rock mass sample. This will lead to inaccurate scanning results, and make it impossible to scan the rock mass sample in all directions during the shear test, thereby failing to meet the visualization requirements of the shearing progressive failure process of the rock mass sample. Through the proposed double horizontal loading devices, the present invention realizes the shear loading of the rock mass sample, and makes the loading cylinder and the rock mass sample staggered to avoid affecting the detection of the rock mass sample by the high-energy accelerator CT scanning. Therefore, the present invention can obtain accurate test results.

Further, the first horizontal loading cylinder 112 includes a first piston assembly 1121 and a first cylinder block assembly 1123. One end of the first piston assembly away from the second bearing device is fixedly provided on the first horizontal loading frame 111, and the other end of the first piston assembly is provided inside the first cylinder block assembly. A first loading cavity 1122 is provided between the first piston assembly and the first cylinder block assembly. The first loading cavity is configured to control a loading force of the first cylinder block assembly on the second bearing device 500 through the injection/return of hydraulic oil. A first static pressure support cavity 1124 is provided at an end of the first cylinder block assembly away from the first piston assembly. The first static pressure support cavity is configured to control the loading force of the first cylinder block assembly on the second bearing device through the injection/return of the hydraulic oil, and reduce a friction generated between the first cylinder block assembly and the second bearing device due to the vertical movement of the second bearing device during the loading process. A distance from a side of the first static pressure support cavity away from the second bearing device to the first piston assembly is smaller than a distance from a side of the first cylinder block assembly away from the first piston assembly to the first piston assembly.

The first horizontal loading cylinder 112 and the second horizontal loading cylinder 122 each are further provided with a vertical limiting device 622 on a side thereof. The vertical limiting device has a limit effect on a cylinder block of the loading cylinder, ensuring that the cylinder block assembly of the cylinder moves horizontally under the action of a corresponding piston assembly. The vertical limiting device also has a guide effect on the second bearing device, ensuring that the dynamic shear box moves in the vertical direction.

Further, a first vertical limiting device and a second vertical limiting device are respectively provided on both sides of the first cylinder block assembly 1123. The first vertical limiting device and the second vertical limiting device are symmetrically provided relative to a length axis of the first cylinder block assembly. The first vertical limiting device and the second vertical limiting device are fixedly provided on an upper part of the second bearing device 500, and the first vertical limiting device and the second vertical limiting device are provided in contact with the first cylinder block assembly.

The second horizontal loading cylinder 122 and the first horizontal loading cylinder 112 are provided in parallel. The second horizontal loading cylinder includes a second piston assembly 1221 and a second cylinder block assembly 1223. One end of the second piston assembly away from the second bearing device is fixedly provided on the second horizontal loading frame 121, and the other end of the second piston assembly is provided inside the second cylinder block assembly. A second loading cavity 1222 is provided between the second piston assembly and the second cylinder block assembly. The second loading cavity is configured to control a loading force of the second cylinder block assembly on the second bearing device 500 through the injection/return of hydraulic oil. A second static pressure support cavity 1224 is provided at an end of the second cylinder block assembly away from the second piston assembly. The second static pressure support cavity is configured to control the loading force of the second cylinder block assembly on the second bearing device through the injection/return of the hydraulic oil, and reduce a friction generated between the second cylinder block assembly and the second bearing device due to the vertical movement of the second bearing device during the loading process. A distance from a side of the second static pressure support cavity away from the second bearing device to the second piston assembly is smaller than a distance from a side of the second cylinder block assembly away from the second piston assembly to the second piston assembly.

Further, a third vertical limiting device and a fourth vertical limiting device are respectively provided on both sides of the second cylinder block assembly 1223. The third vertical limiting device and the fourth vertical limiting device are symmetrically provided relative to a length axis of the second cylinder block assembly. The third vertical limiting device and the fourth vertical limiting device are fixedly provided on the second bearing device, and the third vertical limiting device and the fourth vertical limiting device are provided in contact with the second cylinder block assembly.

In this embodiment, the first bearing device 400 includes a first structure, a second structure and a third structure vertically, which are provided in sequence. The static shear box further includes a first limiting device and a second limiting device. The first limiting device and the second limiting device are respectively provided on an upper side and a lower side of the first rectangular frame. The first limiting device is fixedly provided on an inner side of the first structure. The second limiting device is fixedly provided on an inner side of the third structure. A rectangular protrusive structure is provided on an inner side of the second structure, and the rectangular protrusive structure is adapted to the rectangular through hole of the first rectangular frame. The first structure, the second structure and the third structure are integrally formed or fixedly connected. The first bearing device further includes a fourth structure. The fourth structure is horizontally provided on the inner side of the third structure, and the fourth structure forms an L-shaped structure with the first structure, the second structure and the third structure. The normal loading device 200 is fixedly provided on the top of the fourth structure. Through the L-shaped design of the first bearing device, the present invention realizes the bearing and fixing of the static shear box and the bearing and fixing of the normal loading device (that is, the loading device that applies the shear force), forming the overall loading frame of the rock mass shear test system for high-energy accelerator CT scanning. The present invention has a compact structure, which reduces the floor space of the laboratory.

Further, the first limiting device is a first limiting cushion block 612, and the second limiting device is a second limiting cushion block 613. The first limiting cushion block and the second limiting cushion block are configured to fix the static shear box and provide a reaction force to the static shear box during the shearing process. A horizontal length of the first limiting cushion block and a horizontal length of the second limiting cushion block are not greater than a horizontal length of the first rectangular frame, thereby avoiding interfering with the vertical movement of the second rectangular frame during the shear test of the normal loading device.

Further, a vertical length of a lower side frame of the second rectangular frame 621 is greater than a vertical length of an upper side frame of the second rectangular frame 621. In this way, the present invention enhances the resistance of the second rectangular frame when the second rectangular frame contacts with the normal loading device, preventing the second rectangular frame from being damaged by the normal loading device 200 during the shearing process.

Preferably, the first horizontal loading frame 111 and the second horizontal loading frame 121 have an identical structure. Each of the first horizontal loading frame and the second horizontal loading frame is a self-balancing loading frame.

Preferably, both the static shear box and the dynamic shear box are made of steel.

Further, a first adjusting plate 410 is provided on a side of the first bearing device 400 adjacent to the rock mass sample. A second adjusting plate 510 is provided on a side of the second bearing device 500 adjacent to the rock mass sample. Each of the first adjusting plate and the second adjusting plate is a rectangular plate. The first adjusting plate and the second adjusting plate are respectively adapted to the interior of the first rectangular frame and the interior of the second rectangular frame.

Further, the length and width of the first adjusting plate 410 are consistent with the length and width of an inner side of the first rectangular frame 611; the length and width of the second adjusting plate 510 are consistent with the length and width of an inner side of the second rectangular frame 621.

Alternatively, the size of the first adjusting plate 410 matches the size of the inner side of the first rectangular frame 611, and the size of the second adjusting plate 510 matches the size of the inner side of the second rectangular frame 621. The size of the first adjusting plate and the size of the second adjusting plate may be identical or different, so as to accommodate different sizes and different types of samples.

During the shearing process, the first horizontal loading cylinder 112 and the second horizontal loading cylinder 122 are used to load simultaneously. That is, according to the pressure of the hydraulic oil injected in the first loading cavity 1122 and the second loading cavity 1222, the first cylinder block assembly 1123 and the second cylinder block assembly 1223 simultaneously load the second bearing device 500. Meanwhile, the hydraulic oil injected into the first static pressure support cavity 1124 and the second static pressure support cavity 1224 simultaneously generates a pressure. At this time, the hydraulic oil injected in the first loading cavity generates a leftward thrust (F1) to the first cylinder block assembly, and the hydraulic oil injected in the first static pressure support cavity generates a rightward thrust (F2) to the first cylinder block assembly, where, $0.98F1 \leq F2 \leq 0.99F1$, that is, $F1 > F2$, and the difference between F1 and F2 is adjacent to zero. In the first horizontal loading device, the thrust of the first cylinder block assembly on the second bearing device is transmitted through the contact between the first static pressure support cavity and the second bearing device. The contact between the first static pressure support cavity and the second bearing device is hydraulic oil contact, that is, the thrust of the first horizontal loading device on the second bearing device is mainly provided by the hydraulic oil in the first static pressure support cavity. This ensures that during the shearing process, the friction between the moving second bearing device (i.e., a shear plate) and the first cylinder block assembly is very low, and is smaller than a rolling friction coefficient, so as to realize a real shear force.

At this time, the hydraulic oil injected in the second loading cavity 1222 generates a leftward thrust (F1) to the second cylinder block assembly 1223, and the hydraulic oil injected in the second static pressure support cavity 1224 generates a rightward thrust (F2) to the second cylinder block assembly 1223, where, $0.98F1 \leq F2 \leq 0.99F1$, that is, $F1 > F2$, and the difference between F1 and F2 is adjacent to zero. In the second horizontal loading device, the thrust of the second cylinder block assembly on the second bearing device 500 is transmitted through the contact between the second static pressure support cavity and the second bearing device. The contact between the second static pressure support cavity and the second bearing device is hydraulic oil contact, that is, the thrust of the second horizontal loading device on the second bearing device is mainly provided by the hydraulic oil in the second static pressure support cavity. This ensures that during the shearing process, the friction between the moving second bearing device (i.e., a shear plate) and the second cylinder block assembly is very low, and is smaller than a rolling friction coefficient, so as to realize a real shear force.

In the present invention, the shear force is applied by the normal loading device. The first horizontal loading frame, the first bearing device, the second horizontal loading frame, the first limiting cushion block, the second limiting cushion block and the first rectangular frame are all fixed. The normal loading device presses the second rectangular frame to move simultaneously with the second bearing device. The second bearing device slides relative to the first horizontal loading cylinder and the second horizontal loading cylinder.

Although the present invention is described with reference to the preferred embodiments, various modifications may be made to the present invention and the components therein may be replaced with equivalents without departing from the scope of the present invention. In particular, the various technical features mentioned in the various embodiments may be combined in any manner in case of no structural conflict. The present invention is not limited to the specific embodiments disclosed herein, but includes all technical solutions falling within the scope of the claims.

It should be noted that in the description of the present invention, terms such as "central", "upper", "lower", "left", "right", "vertical", "horizontal", "inner" and "outer" indicate orientation or position relationships based on the accompanying drawings. They are merely intended to facilitate description, rather than to indicate or imply that the mentioned device or components must have the specific orientation and must be constructed and operated in the specific orientation. Therefore, these terms should not be construed as a limitation to the present invention. Moreover, the terms "first", "second" and "third" are used only for the purpose of description and are not intended to indicate or imply relative importance.

It should be noted that in the description of the present invention, unless otherwise clearly specified, meanings of terms "install", "connect with" and "connect to" should be understood in a broad sense. For example, the connection may be a fixed connection, a removable connection, or an integral connection; may be a mechanical connection or an electrical connection; may be a direct connection or an indirect connection via a medium; or may be an internal connection between two components. Those skilled in the art should understand the specific meanings of the above terms in the present invention based on specific situations.

In addition, terms "include", "comprise", or any other variations thereof are intended to cover non-exclusive inclusions, so that a process, an article, or a device/apparatus including a series of elements not only includes those elements, but also includes other elements that are not explicitly listed, or also includes inherent elements of the process, the article or the device/apparatus.

The technical solutions of the present invention are described with reference to the preferred implementations and accompanying drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions after these changes or substitutions should fall within the protection scope of the present invention.

What is claimed is:

1. A rock mass shear test system for high-energy accelerator computed tomography (CT) scanning, comprising:
a shear box for accommodating a rock mass sample,
a bearing device for supporting the shear box, and
a shear loading device;
wherein the shear box comprises a static shear box and a dynamic shear box;
the static shear box and the dynamic shear box are provided opposite to each other from left to right;
the static shear box comprises a first rectangular frame, and the dynamic shear box comprises a second rectangular frame;
the second rectangular frame is opposite to the first rectangular frame;
the bearing device comprises a first bearing device and a second bearing device;
the first bearing device is provided on an outer side of the static shear box;
the first rectangular frame is fixedly provided on an inner side of the first bearing device;
the first bearing device and the first rectangular frame constitute a left-half accommodating cavity with a right opening;
the second bearing device is provided on an outer side of the dynamic shear box;
the second rectangular frame is fixedly provided on an inner side of the second bearing device;
the second bearing device is provided with a protrusive structure extending into the second rectangular frame;
the second bearing device and the second rectangular frame constitute a right-half accommodating cavity with a left opening;
the shear loading device comprises a horizontal loading device and a normal loading device;
the horizontal loading device comprises a first horizontal loading device and a second horizontal loading device;
the first horizontal loading device comprises a first horizontal loading frame and a first horizontal loading cylinder;
the first horizontal loading frame is provided with a first rectangular through hole;
an upper side surface of the first bearing device is connected to a left side wall of the first rectangular through hole;
the first horizontal loading cylinder is connected to a right side wall of the first rectangular through hole;
the first horizontal loading cylinder is configured to apply a first horizontal loading force to the second bearing device under an action of a hydraulic pressure;
the second horizontal loading device comprises a second horizontal loading frame and a second horizontal loading cylinder;
the second horizontal loading frame is provided with a second rectangular through hole;
a middle side surface of the first bearing device is connected to a left side wall of the second rectangular through hole;
the second horizontal loading cylinder is connected to a right side wall of the second rectangular through hole;
the second horizontal loading cylinder is configured to apply a second horizontal loading force to the second bearing device under the action of the hydraulic pressure;
the normal loading device is provided under the second rectangular frame;
a movable end of the normal loading device is provided in contact with the second rectangular frame;
wherein during a shearing process, the first horizontal loading cylinder and the second horizontal loading cylinder apply a horizontal loading force to the rock mass sample through the second bearing device; the normal loading device, under an action of a driving force, presses the second rectangular frame, the second bearing device and a rock mass sample placed inside the second rectangular frame to move upward relative to a rock mass sample placed inside the first rectangular frame, and a shear test of the rock mass sample is performed;
wherein the rock mass shear test system further comprises a high-energy accelerator CT scanning system and a rotating device;
the high-energy accelerator CT scanning system comprises a ray source device and a detector device;
the ray source device and the detector device are respectively provided on both sides of the rock mass sample;
the ray source device and the detector device are configured to detect a progressive failure process of incubation, initiation, propagation and penetration of cracks of the rock mass sample in the shear test;
a height of the ray source device is h, a height of the first horizontal loading cylinder is h1, and a height of the second horizontal loading cylinder is h2, wherein h∈(h2, h1);
the rotating device is provided under the bearing device and the normal loading device;
the rotating device is driven by a rotating power device to drive the loading device and the bearing device to rotate with the shear box, and cooperate with the high-energy accelerator CT scanning system to accurately acquire time and space information of generation and development of cracks in a shearing progressive failure process of a rock mass.

2. The rock mass shear test system for the high-energy accelerator CT scanning according to claim 1, wherein
the first horizontal loading cylinder comprises a first piston assembly and a first cylinder block assembly;
a first end of the first piston assembly is fixedly provided on the first horizontal loading frame, and a second end of the first piston assembly is provided inside the first cylinder block assembly, wherein the first end of the first piston assembly is away from the second bearing device;
a first loading cavity is provided between the first piston assembly and the first cylinder block assembly;
the first loading cavity is configured to control a loading force of the first cylinder block assembly on the second bearing device through an injection/return of a hydraulic oil;
a first static pressure support cavity is provided at an end of the first cylinder block assembly, wherein the end of the first cylinder block assembly is away from the first piston assembly;
the first static pressure support cavity is configured to control the loading force of the first cylinder block assembly on the second bearing device through the injection/return of the hydraulic oil, and reduce a friction generated between the first cylinder block assembly and the second bearing device due to a vertical movement of the second bearing device during a loading process;
a distance from a side of the first static pressure support cavity to the first piston assembly is smaller than a distance from a side of the first cylinder block assembly to the first piston assembly, wherein the side of the first static pressure support cavity is away from the second bearing device, and the side of the first cylinder block assembly is away from the first piston assembly;

a first vertical limiting device and a second vertical limiting device are respectively provided on both sides of the first cylinder block assembly;

the first vertical limiting device and the second vertical limiting device are symmetrically provided relative to a length axis of the first cylinder block assembly;

the first vertical limiting device and the second vertical limiting device are fixedly provided on an upper part of the second bearing device; and the first vertical limiting device and the second vertical limiting device are provided in contact with the first cylinder block assembly.

3. The rock mass shear test system for the high-energy accelerator CT scanning according to claim 2, wherein the second horizontal loading cylinder and the first horizontal loading cylinder are provided in parallel;

the second horizontal loading cylinder comprises a second piston assembly and a second cylinder block assembly;

a first end of the second piston assembly is fixedly provided on the second horizontal loading frame, and a second end of the second piston assembly is provided inside the second cylinder block assembly, wherein the first end of the second piston assembly is away from the second bearing device;

a second loading cavity is provided between the second piston assembly and the second cylinder block assembly;

the second loading cavity is configured to control a loading force of the second cylinder block assembly on the second bearing device through the injection/return of the hydraulic oil;

a second static pressure support cavity is provided at an end of the second cylinder block assembly, wherein the end of the second cylinder block assembly is away from the second piston assembly;

the second static pressure support cavity is configured to control the loading force of the second cylinder block assembly on the second bearing device through the injection/return of the hydraulic oil, and reduce a friction generated between the second cylinder block assembly and the second bearing device due to the vertical movement of the second bearing device during the loading process;

a distance from a side of the second static pressure support cavity to the second piston assembly is smaller than a distance from a side of the second cylinder block assembly to the second piston assembly, wherein the side of the second static pressure support cavity is away from the second bearing device, and the side of the second cylinder block assembly is away from the second piston assembly;

a third vertical limiting device and a fourth vertical limiting device are respectively provided on both sides of the second cylinder block assembly;

the third vertical limiting device and the fourth vertical limiting device are symmetrically provided relative to a length axis of the second cylinder block assembly;

the third vertical limiting device and the fourth vertical limiting device are fixedly provided on a lower part of the second bearing device; and the third vertical limiting device and the fourth vertical limiting device are provided in contact with the second cylinder block assembly.

4. The rock mass shear test system for the high-energy accelerator CT scanning according to claim 3, wherein a first adjusting plate is provided on a side of the first bearing device, wherein the side of the first bearing device is adjacent to the rock mass sample;

a second adjusting plate is provided on a side of the second bearing device, wherein the side of the second bearing device is adjacent to the rock mass sample;

each of the first adjusting plate and the second adjusting plate is a rectangular plate; and the first adjusting plate and the second adjusting plate are respectively adapted to an interior of the first rectangular frame and an interior of the second rectangular frame.

5. The rock mass shear test system for the high-energy accelerator CT scanning according to claim 2, wherein a first adjusting plate is provided on a side of the first bearing device, wherein the side of the first bearing device is adjacent to the rock mass sample;

a second adjusting plate is provided on a side of the second bearing device, wherein the side of the second bearing device is adjacent to the rock mass sample;

each of the first adjusting plate and the second adjusting plate is a rectangular plate; and the first adjusting plate and the second adjusting plate are respectively adapted to an interior of the first rectangular frame and an interior of the second rectangular frame.

6. The rock mass shear test system for the high-energy accelerator CT scanning according to claim 1, wherein the first bearing device comprises a first structure, a second structure and a third structure, wherein the first structure, the second structure and the third structure are provided in sequence;

the static shear box further comprises a first limiting device and a second limiting device;

the first limiting device and the second limiting device are respectively provided on an upper side and a lower side of the first rectangular frame;

the first limiting device is fixedly provided on an inner side of the first structure;

the second limiting device is fixedly provided on an inner side of the third structure;

a rectangular protrusive structure is provided on an inner side of the second structure, and the rectangular protrusive structure is adapted to the rectangular through hole of the first rectangular frame;

the first structure, the second structure and the third structure are integrally formed or fixedly connected.

7. The rock mass shear test system for the high-energy accelerator CT scanning according to claim 6, wherein the first bearing device further comprises a fourth structure;

the fourth structure is horizontally provided on the inner side of the third structure;

the fourth structure forms an L-shaped structure with the first structure, the second structure and the third structure; and the normal loading device is fixedly provided on a top of the fourth structure.

8. The rock mass shear test system for the high-energy accelerator CT scanning according to claim 7, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

9. The rock mass shear test system for the high-energy accelerator CT scanning according to claim 6, wherein
- the first limiting device is a first limiting cushion block;
- the second limiting device is a second limiting cushion block;
- the first limiting cushion block and the second limiting cushion block are configured to fix the static shear box and provide a reaction force to the static shear box during the shearing process;
- a horizontal length of the first limiting cushion block and a horizontal length of the second limiting cushion block are smaller than or equal to a horizontal length of the first rectangular frame.

10. The rock mass shear test system for the high-energy accelerator CT scanning according to claim 9, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

11. The rock mass shear test system for the high-energy accelerator CT scanning according to claim 6, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

12. The rock mass shear test system for the high-energy accelerator CT scanning according to claim 1, wherein
- a vertical length of a lower side frame of the second rectangular frame is greater than a vertical length of an upper side frame of the second rectangular frame.

13. The rock mass shear test system for the high-energy accelerator CT scanning according to claim 12, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

14. The rock mass shear test system for the high-energy accelerator CT scanning according to claim 1, wherein
- the first horizontal loading frame and the second horizontal loading frame have an identical structure; and
- each of the first horizontal loading frame and the second horizontal loading frame is a self-balancing loading frame.

15. The rock mass shear test system for the high-energy accelerator CT scanning according to claim 14, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

16. The rock mass shear test system for the high-energy accelerator CT scanning according to claim 1, wherein
- a first adjusting plate is provided on a side of the first bearing device, wherein the side of the first bearing device is adjacent to the rock mass sample;
- a second adjusting plate is provided on a side of the second bearing device, wherein the side of the second bearing device is adjacent to the rock mass sample;
- each of the first adjusting plate and the second adjusting plate is a rectangular plate; and
- the first adjusting plate and the second adjusting plate are respectively adapted to an interior of the first rectangular frame and an interior of the second rectangular frame.

* * * * *